United States Patent
Perssson

(10) Patent No.: US 8,236,007 B2
(45) Date of Patent: Aug. 7, 2012

(54) VOICE PROSTHESIS, INSERTION TOOL AND METHOD

(75) Inventor: Jan-Ove Persson, Höör (SE)

(73) Assignee: Atos Medical AB, Horby (SE)

( * ) Notice: Subject to any disclaimer, the term of this patent is extended or adjusted under 35 U.S.C. 154(b) by 424 days.

(21) Appl. No.: 11/813,393

(22) PCT Filed: Dec. 15, 2005

(86) PCT No.: PCT/SE2005/001924
§ 371 (c)(1), (2), (4) Date: May 2, 2008

(87) PCT Pub. No.: WO2006/073340
PCT Pub. Date: Jul. 13, 2006

(65) Prior Publication Data
US 2009/0043386 A1 Feb. 12, 2009

(30) Foreign Application Priority Data
Jan. 7, 2005 (SE) ...................................... 0500038

(51) Int. Cl.
A61F 11/00 (2006.01)
(52) U.S. Cl. ...................................... 606/108
(58) Field of Classification Search ............ 606/108; 623/9; 128/200.26, 207.14, 207.15, 207.16, 128/207.17, 207.29
See application file for complete search history.

(56) References Cited

U.S. PATENT DOCUMENTS

| | | | |
|---|---|---|---|
| 4,614,516 A | 9/1986 | Blom et al. | |
| 5,064,433 A | 11/1991 | Blom et al. | |
| 5,314,470 A | 5/1994 | Persson | |
| 5,578,083 A | 11/1996 | Laguette et al. | |
| 5,935,165 A * | 8/1999 | Schouwenburg | 623/9 |
| 5,976,151 A * | 11/1999 | Siegbahn | 606/108 |
| 6,527,780 B1* | 3/2003 | Wallace et al. | 606/108 |
| 6,666,208 B1 | 12/2003 | Schumacher et al. | |
| 6,776,797 B1 | 8/2004 | Blom et al. | |
| 2002/0133168 A1* | 9/2002 | Smedley et al. | 606/108 |
| 2004/0204759 A1 | 10/2004 | Blom et al. | |

FOREIGN PATENT DOCUMENTS

| | | |
|---|---|---|
| DE | 198 43 280 | 5/2000 |
| EP | 0 735 844 | 9/1997 |
| WO | WO 97/45075 | 12/1997 |

* cited by examiner

*Primary Examiner* — Gary Jackson
*Assistant Examiner* — Jonathan Hollm
(74) *Attorney, Agent, or Firm* — Merchant & Gould P.C.

(57) ABSTRACT

An insertion tool for inserting a tracheostoma voice prosthesis member into a fistula between oesophagus and trachea. The insertion tool includes an engagement portion for engaging and retaining said tracheostoma voice prosthesis member to be inserted into the fistula, a gripping portion for gripping a safety strap of said member in a firm grip, a shaft portion adapted to be held by one hand of a user, and a release lever arrangement adjacent said shaft portion for operation by a finger of the same hand as is holding said shaft portion, whereby said release lever, after said member being positioned in place in said fistula by operation of said insertion tool by means of said shaft, is adapted to be operated for releasing said member by one-hand operation. A tracheostoma voice prosthesis member and a method for applying said tracheostoma voice prosthesis member are also provided.

1 Claim, 7 Drawing Sheets

VOICE PROSTHESIS, INSERTION TOOL AND METHOD

FIELD OF THE INVENTION

This invention pertains to a voice prosthesis for persons whose larynx has been removed, an insertion tool for the prosthesis and a method of insertion of the voice prosthesis by means of the insertion tool.

BACKGROUND OF THE INVENTION

As a result of different diseases, the larynx of the diseased must sometimes be removed by surgery. The trachea is attached to the neck forming a so called tracheostoma or an artificial opening into the trachea leading out into the front portion of the neck, so as to make possible breathing. Due to these measures the ability to speak is lost.

In order to restore the ability of speech to a certain extent, it is possible, by means of surgery, to open a fistula between the oesophagus and the trachea to direct air from the lungs, through the fistula and to the oral cavity. This fistula must always be closed, except when air is admitted into the pharynx, because food and liquids entering the oesophagus through the mouth must be prevented from entering the trachea and further into the lungs. For this purpose, a voice prosthesis member may be inserted into the fistula. The voice prosthesis member may comprise a tubular element having a through hole and a one-way valve. A retaining member ensures that the prosthesis is kept in place. The one-way valve permits air to pass from the trachea to the oesophagus when a certain opening pressure has been reached in the trachea, but it is completely closed in the reverse direction. By temporarily closing the tracheostoma, air may be directed to flow, under the pressure of the lungs, through the hole of the voice prosthesis member into the pharynx, so that the user is able to speak. A voice prosthesis of this type is, for instance, disclosed in U.S. Pat. No. 5,578,083.

However, a device of this type has a relatively small inner diameter in relation to the outer diameter, so that it from an efficiency point of view is not optimal. More precisely, it is important to have as large smallest inner diameter as possible in order to allow high airflows through the prosthesis. A large smallest inner diameter of the prosthesis also considerably improves the quality of voice produced by the user. On the other hand, it is desired that the outer diameter of the prosthesis is as small as possible due to the requirement that the fistula should not be too large, as otherwise complications may occur.

U.S. Pat. No. 5,314,470 discloses a voice prosthesis with an integrated support ring. The support ring serves as a seat for the one-way valve, which is of the flap valve type. The ring is located in close proximity to the valve while the other walls of the voice prosthesis are relatively thick in order to withstand forced induced by the fistula and to ensure that the fistula does not collapse when the voice prosthesis is in place. Therefore, the voice prosthesis disclosed in U.S. Pat. No. 5,314,470 does not have an optimal ratio between maximal outer diameter of the through passage and the smallest inner diameter of the voice prosthesis. The voice prosthesis according to U.S. Pat. No. 5,314,470 is of the so-called in-dwelling type, which is inserted more or less permanently by a surgeon. It is normally not removed, but is cleaned in place. The prosthesis has relatively rigid flanges, which keeps the prosthesis firmly in place.

Another type of voice prosthesis is of the so-called non-indwelling type, which may be removed for cleaning and then reinserted by the user.

During this procedure, there is a risk, especially when the user performs the removal or insertion of the prosthesis, that the prosthesis is dropped into the oesophagus, which is less dangerous as the prosthesis most often passes the intestines without problem, or into the trachea, which may be a major problem for the user. When such a dropped prosthesis reaches the lungs, it may have to be removed by surgery. Therefore, some previously known voice prosthesis are equipped with safety straps that remain attached to the prosthesis after insertion, and which are led out of the stoma and taped to the skin of the user. However, one problem related with these straps is frequent leakage of respiratory gases passing under or beneath the tape. Another problem is that insertion of the prosthesis, which often is done by means of an insertion tool onto which the prosthesis is releasably attached, is cumbersome for the user, since the user has to control both the positioning of the prosthesis in the fistula and the strap requiring the use of two hands, see for example U.S. Pat. No. 5,064,433.

Thus, there is a need for a new and improved voice prosthesis, as well as an improved insertion tool therefore and a related insertion method.

SUMMARY OF THE INVENTION

Accordingly, the present invention seeks to mitigate, alleviate or eliminate one or several of the above-identified deficiencies and disadvantages in the art, taken singly or in any combination and solves at least the above mentioned problems by providing a voice prosthesis, an voice prosthesis insertion tool and a method for inserting a voice prosthesis according to the appended patent claims.

According to one aspect of the invention, there is provided a tracheostoma voice prosthesis member intended for insertion into a fistula between the oesophagus and the trachea. The member comprises a tubular body portion with a proximal end intended to open into the trachea and a distal end intended to open into the oesophagus; a one-way flap valve covering a through opening of the tubular body portion for allowing air to pass through the tubular body portion from the proximal end to the distal end but preventing air and other matter from passing from the distal end to the proximal end; and a safety strap integral with the tubular body portion at the proximal end thereof and extending substantially in the radial direction. According to the invention, the safety strap has a substantially reduced material thickness at the longitudinal edges thereof.

The safety strap may have a thickness at the edges of less than 50%, such as less than 30%, compared to the maximum thickness of the safety strap. The maximum thickness may be about 1 mm. The ratio between the smallest inner diameter of the through opening and the largest outer diameter of the tubular body portion may be larger than about 58%.

In an embodiment, the member further comprises a support ring for supporting the one-way valve and/or stiffening the tubular body portion adjacent the one-way valve. The support ring may be arranged between the one-way valve and the proximal end of the tubular body portion. The tubular body portion may have a substantially constant outer diameter and the smallest inner diameter is arranged at the support ring.

In another embodiment, the one-way valve may be arranged adjacent the distal end of the tubular body portion. The one-way valve may be an integral part of the tubular body portion and may be made in a single piece with the tubular body portion. The support ring may be substantially cylindrical and may have a length, which is substantially equal to or larger than the largest external diameter thereof. The support ring may have a flange at the distal end thereof facing the circular plate and forming a seat for the valve plate. The tubular body portion may at the inner periphery be provided with a recess with enlarged inner diameter for encompassing the support ring. The tubular body portion may comprise a distal annular flange adjacent the distal end of the tubular body portion and a proximal annular flange adjacent the proximal end of the body portion for encompassing a wall part of the fistula between the flanges. The tubular body portion may be extended, in the distal direction, beyond the distal flange. The tubular body portion and one-way valve may be made of en elastomeric material, such as silicon or polyurethane. The support ring may be made of a rigid material, such as PVDF pr PTFE.

In a further embodiment, the member may further comprise a safety medallion attached to the member and having a dimension sufficiently large for preventing the member from falling down in the trachea. The medallion may be attached to the member via a cord, e.g. made of polypropylene.

According to another aspect of the invention, there is provided an insertion tool for inserting a tracheostoma voice prosthesis member into a fistula between oesophagus and trachea. The tool comprises an engagement portion for engaging and retaining a member to be inserted in the fistula; a gripping portion for gripping a safety strap of the member in a firm grip; a shaft portion adapted to be held by one hand of a user; a release lever arranged adjacent the shaft portion for operation by a finger of the same hand as is holding the shaft portion; whereby the release lever, after being positioned in place in the fistula by operation of the insertion tool by means of the shaft, is adapted to be operated for releasing the member by one-hand operation.

According to yet another aspect of the invention, there is provided a method for placing a tracheostoma voice prosthesis member into a fistula between oesophagus and trachea by means of an insertion tool, comprising: engaging the member by means of an engagement portion of the tool; gripping a safety strap of the member by a gripping portion of the tool; placing the member in position in the fistula by operating a shaft portion of the tool adapted to be held by one hand of a user; releasing the safety strap by operating a release lever arranged adjacent the shaft portion for operation by a finger of the same hand as is holding the shaft portion.

The present invention has the advantage over the prior art that it reduces possible complications related to voice prosthesis. Furthermore, the voice prosthesis according to the invention makes possible a better speech quality than conventional voice prosthesis.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION OF EMBODIMENTS OF THE INVENTION

The following description focuses on a particular embodiment of the present invention. However, it will be appreciated that the invention is not limited to this embodiment.

Figure 1:
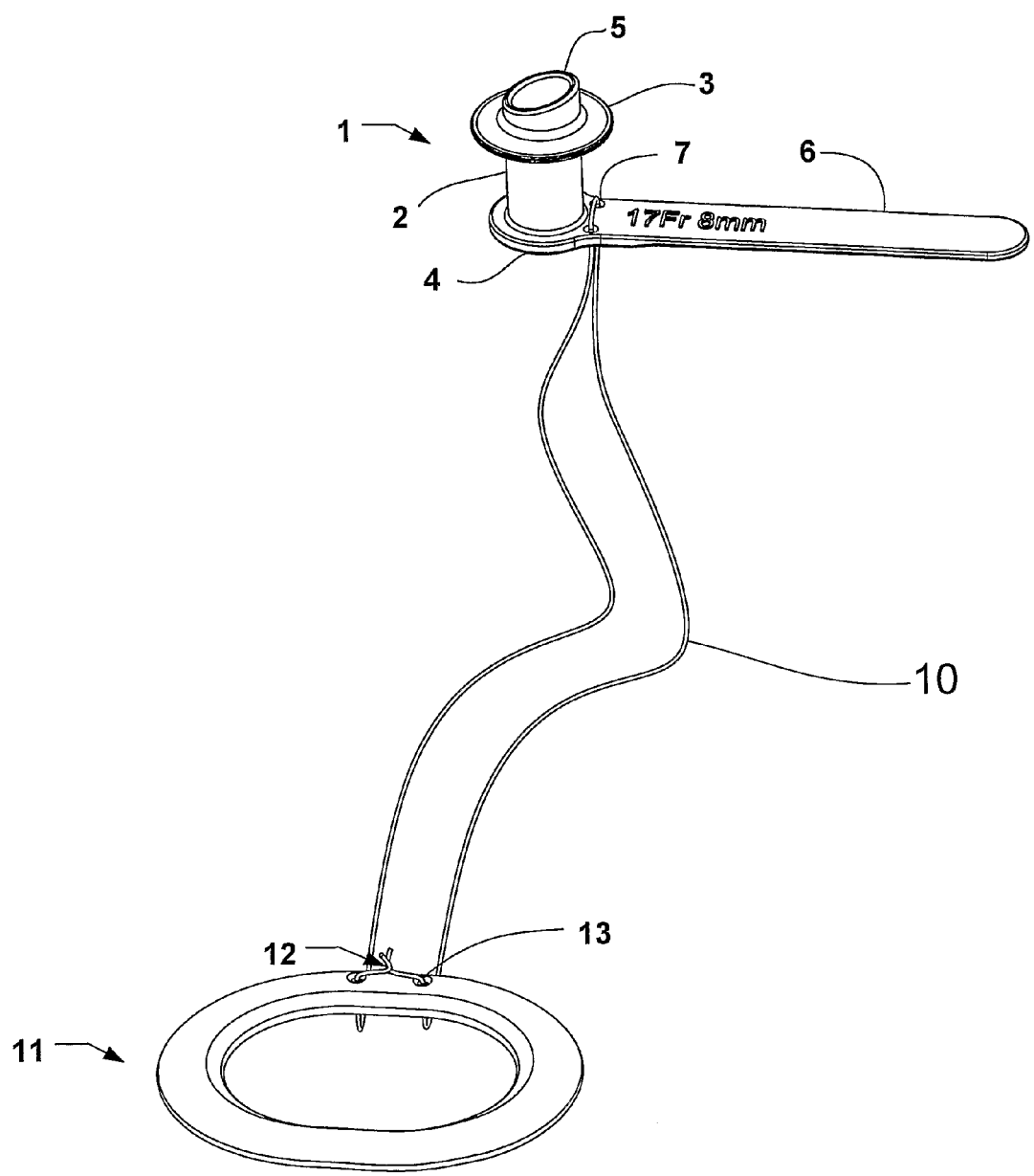
FIG. 1 is a schematic isometric view illustration of an embodiment of the voice prosthesis and a safety ring attached thereto.

FIG. 1 is an isometric view of a voice prosthesis according to the invention. The voice prosthesis 1 comprises a tubular body portion 2, which may have a substantially cylindrical outer surface. A distal flange 3 is arranged adjacent a distal end of the tubular body portion and a proximal flange 4 is arranged adjacent the proximal end of the tubular portion. The tubular body portion extends beyond the distal flange by a distal end portion 5 as shown in FIG. 1. The end portion 5 is cut along an inclined surface in relation to the longitudinal axis of the tubular portion.

The entire voice prosthesis is made from an elastic material. The flanges are made sufficiently thin so that they may yield when the voice prosthesis is inserted by the user.

A safety strap 6 extends from the proximal flange as en elongation thereof. A safety medallion 11 is attached to the proximal flange 4 by means of a strong cord 10. The proximal flange 4 is provided with two holes 7 and the medallion is provided with two holes 13. The cord 10 passes through said holes and the medallion is retained by a knot 12 or similar.

In one embodiment of the present invention the safety strap 6 extends from the proximal flange 4 in a substantially radial direction.

Figure 3A:
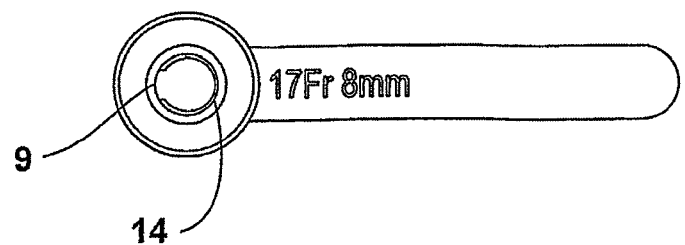
FIG. 3A-3C are illustrations of the embodiment of the voice prosthesis, revealing more details.
Figure 3B:
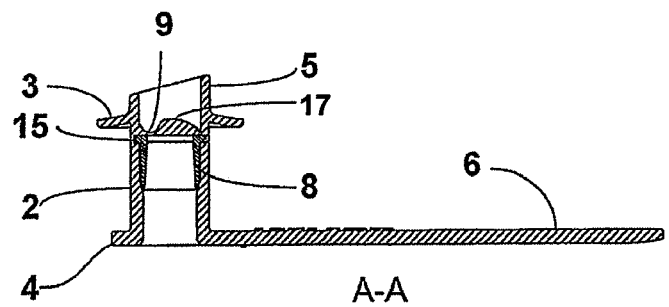

With reference to FIG. 3B, a flap valve in the nature of a valve plate 7 is arranged inside the tubular body portion 2. The valve plate is connected to the body portion by a hinge portion 9. The rest of the plate is free from the tubular body portion and a peripheral ring-shaped space 14 is formed between the valve plate and the inner surface of the tubular body portion as appears from FIG. 3A. The valve plate may be formed integrally in one piece with the tubular body portion during injection moulding of said parts. The valve plate has a substantially flat proximal bottom surface and a dome-shaped distal surface as appears from FIG. 3B.

The valve plate is supported by a valve seat in the nature of a support ring 8. The support ring is formed of a material, which is stiffer than the remaining voice prosthesis. The support ring has a substantially flat distal surface facing the valve plate 17. The distal end of the support ring 8 is provided with an outer flange 15, which engages a recess in the wall of the tubular body portion. As appears from FIG. 3C, the wall thickness of the tubular body portion is reduced to form a recess, in which the support ring is positioned and attached, for example by gluing. The support ring has a substantially cylindrical inner surface, which is slightly conical with the smallest diameter at the distal end, adjacent the flange 15. The outer surface of the support ring may also be slightly conical with the smallest diameter at the proximal end. In this way, the support ring can be easily injection molded or turned. The support ring is made from a material, which makes it possible to manufacture thin constructions, such as PVDF or PTFE.

Figure 2:
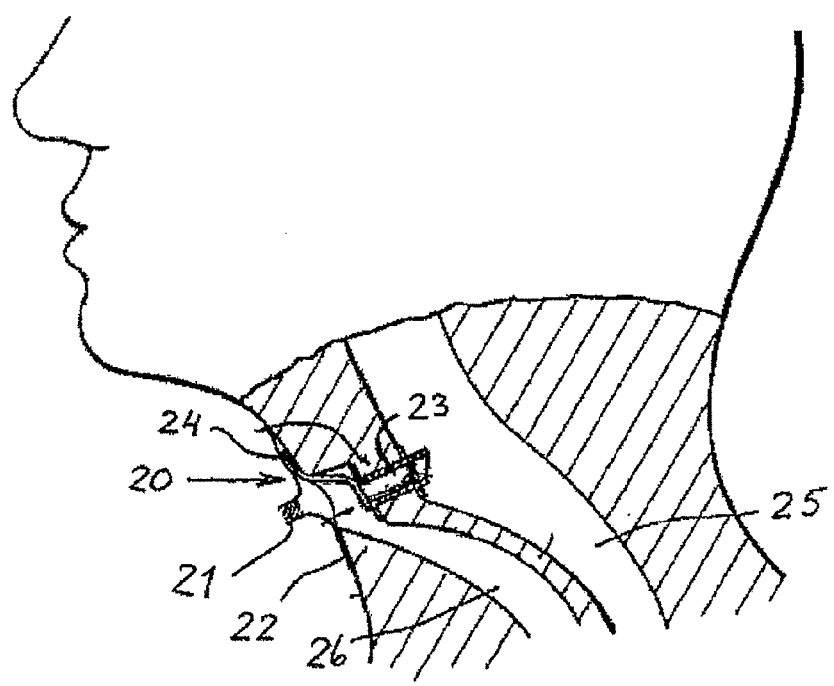
FIG. 2 is a schematic illustration of the anatomical position of a voice prosthesis.

As shown in FIG. 2, as a result of different diseases, the larynx of a person must sometimes be removed by surgery.

The trachea is attached to the neck forming a so called tracheostoma or an artificial opening 20 into the trachea from the front portion of the neck, so as to make possible breathing. A filter 21 may be arranged in the opening as is described in EP 0735844. The filter is attached to the skin of the neck by an adhesive disk 22.

A voice prosthesis 1 according to the invention is arranged in a fistula 23 surgically created in the wall between oesophagus and trachea of a person provided with a tracheostoma. Flanges 3 and 4 encompass the wall and ensure that the voice prosthesis is maintained in place once inserted. The safety strap 6 of the voice prosthesis is passed along the surface of the tracheostoma and to the outer surface of the neck. A plaster 24 attaches the safety strap to the skin surface. Other attachment means may be used, such as a tape or an adhesive. The attachment means should be of such a type that the skin is not being irritated.

The expressions "proximal" and "distal" relates to the voice prosthesis as arranged in place as shown in FIG. 2, so that the distal end is the end opening into oesophagus 25 and the proximal end is the end opening into trachea 26.

Figure 3C:
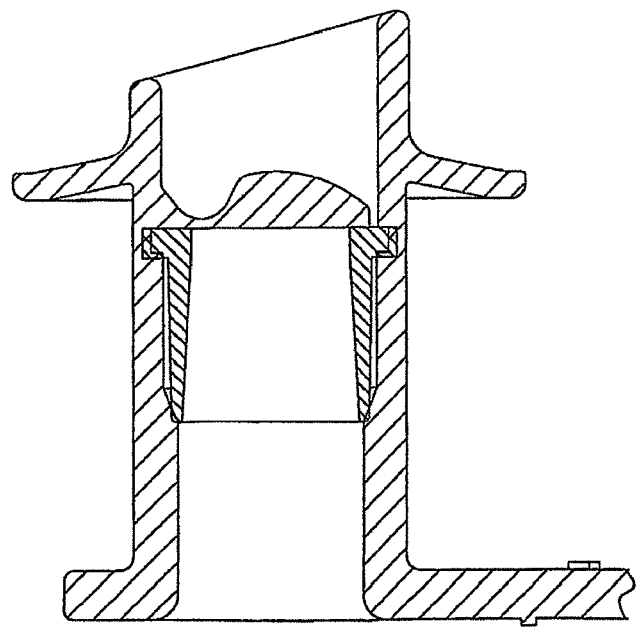

FIGS. 3B and 3C are cross-sectional views of the voice prosthesis according to an embodiment of the invention. As appears, the hinge portion 9 is arranged approximately above the inner edge of the support ring. The periphery of valve plate rests on the ring-shaped edge of the support ring, which forms the valve seat for the valve plate. When a pressure is provided from the proximal end, the valve plate moves away from the valve seat under the influence of the airflow and passes the airflow there through. However, when a pressure is provided from the distal end, the valve plate is firmly pressed towards the valve seat and no air or other matter is permitted to pass beyond the valve plate. Because of the dome shape, the valve plate is able to withstand substantial pressure in the reverse direction.

As appears from FIG. 3C, the distal flange is angled somewhat downward in order to make it more easy to insert the voice prosthesis. The proximal flange may be angled in the opposite direction, so that the wall of the fistula is retained between the flanges.

The support ring forms a valve seat for the valve plate but also forms reinforcement for the tubular body portion so that it can withstand movements and forces from the fistula. For safe operation of the one-way valve, the inner opening of the tubular body portion must not be deformed. The valve plate 7 must always be free to move and the ring-shaped space 14 must not be compromised. The support ring ensures that the valve plate may always operate in the correct way.

The length of the support ring may be approximately the same as the diameter of the flange of the support ring. Alternatively, the length is larger than the diameter.

The rest of the tubular body portion is made with a wall thickness, which is sufficient for withstanding the forces exerted by the fistula. The tubular body portion can still operate satisfactory even if it is somewhat distorted, but the through open area should not be decreased too much. In the embodiment shown, the smallest area of the passage through the tubular body portion is the seat area of the support ring.

The distal end portion 5 of the tubular body portion extends into the oesophagus. The longest portion is facing upwards. If food matter or other matter comes close to the voice prosthesis, the distal end portion 5 will to a certain extent prevent entry of such matter into the tubular body portion.

The safety strap 6 also faces upwards and is positioned as shown in FIG. 2.

The tubular body portion may have different length in dependence of the wall thickness of the fistula of the user. Moreover, the overall diameter of the tubular body portion may be of different sizes. Examples of dimensions appears from the following table 1:

TABLE 1

|  | Outer diameter over the body (between the flanges) | | Smallest inner diameter, Support ring | |
| --- | --- | --- | --- | --- |
|  | Size (Fr) | Size (mm) | Diameter (mm) | Ratio |
| Provox | 22 | 7.5 | 3.9 | 52% |
| Provox2 | 22.5 | 7.5 | 3.9 | 52% |
| Provox NID 17 | 17 | 5.67 | 3.3 | 58% |
| Provox NID 20 | 20 | 6.67 | 4.1 | 61% |

Provox and Provox2 are prostheses according to prior art sold by Applicant.

As appears from the table indicated above, the inner diameter is as large as possible in relation to the outer diameter of the tubular body portion. The relation between the smallest inner diameter and the largest outer diameter is equal to or larger than 58%. In this way it is assured that the tubular body portion is sufficiently rigid in spite of being manufactured by a soft and pliable material. The support ring is arranged in a portion having reduced wall thickness of the tubular body portion, but the support ring supports the tubular body portion so that it is not deformed. Thus, the voice prosthesis is optimized for low speaking resistance.

This is also shown by the comparative examples given in table 2, below:

TABLE 2

|  | Airflow in l/min | pressure drop in kPa |
| --- | --- | --- |
| 16 Fr prosthesis, other brand | 10 | 1.40 |
| Provox NID 17 | 10 | 0.80 |
| 16 Fr prosthesis, other brand | 20 | 3.50 |
| Provox NID 17 | 20 | 2.30 |

The safety strap 6 has a substantially constant width and has a length, which is sufficient for reaching out from the fistula through the tracheostoma to the outside skin surface of the neck of the user, where it is attached by means of a plaster or similar means.

During normal operation, the user breathes through the tracheostoma as usual. If the user wants to use the voice prosthesis, the user closes the opening of the tracheostoma, for example by putting a finger over the opening of the filter 21. Then, the air expelled by the lungs has to pass through the voice prosthesis and into the oesophagus as appears from FIG. 2. The airflow can be formed into words by normal re-shaping of the oral cavities as occurs during normal speech.

A problem with previous similar voice prosthesis is that air may leek along the safety strap and escape. This problem is solved in the present invention by shaping the safety strap with a flat distal surface and a dome-shaped or rounded proximal surface. The distal surface faces the skin of the user and conforms easily to the skin surface. The plaster passes over the dome-shaped outer surface and presses the safety strap firmly towards the skin. In this way, no air channels are formed through which the air may escape. Thus, the voice prosthesis becomes tight and no air will leek during operation.

Figure 4:
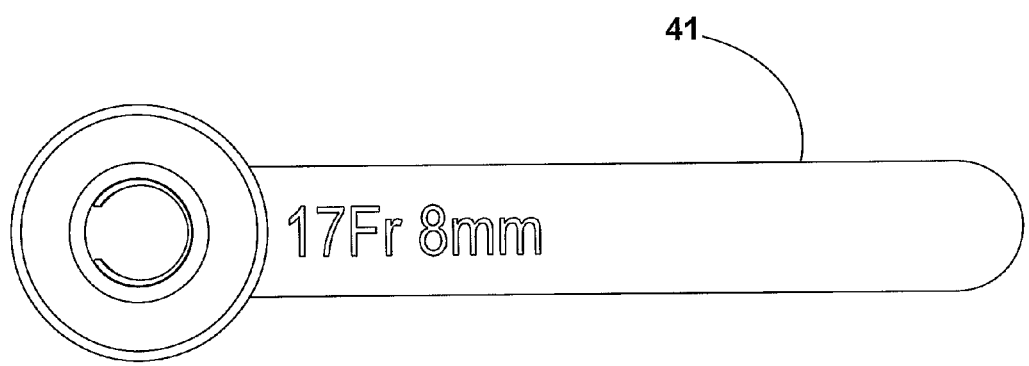
FIG. 4 is a further detailed illustrations of the safety strap of the voice prosthesis.

The shape of the safety strap is shown in FIG. 4. The distal surface is the surface shown in FIG. 4 and is provided with indications of the size of the voice prosthesis, in this case 17 Fr 8 mm, which means that the outer diameter of the tubular body portion is 8 mm. The distal surface 41 is substantially flat. The opposite surface or proximal surface is dome-shaped in cross-section so that the plaster will press the flat surface securely towards the skin in use. The cross-sectional surface is the same over the length of the safety strap except at the end, where it is rounded off, as appears from FIGS. 3A and 3B.

Figure 6:
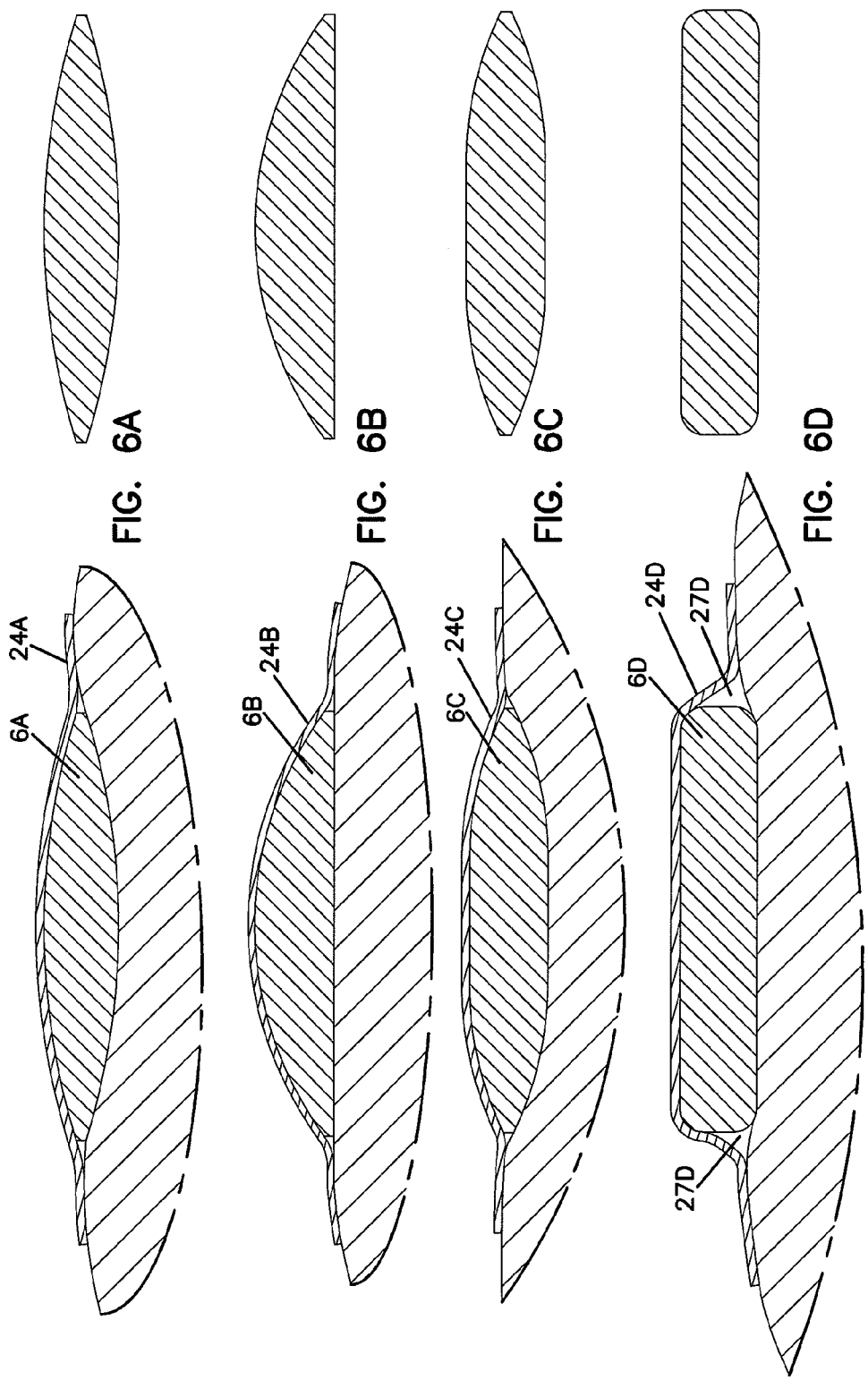
FIG. 6A-6D are cross-sectional views of the safety strap.

FIGS. 6A-6D show different designs of the safety strap 6A-6D. FIG. 6D shows the previously known device. The safety strap 6D has a substantially rectangular cross-section. A plaster 24D would not be able to completely seal the area between the safety strap 6D and the plaster 24D and two channels 27D are formed as shown. The channels extend from the voice prosthesis and along the safety strap, Air may pass along the channels and escape to the surrounding atmosphere. Such leaking air may cause disturbing noise and will also reduce the efficiency of the voice prosthesis.

The design described above corresponds to FIG. 6B, in which the surface facing the skin (the distal surface) is substantially flat or plane and the opposite surface is dome-shaped or convex. A plaster 24B forces the flat surface towards the skin and almost no channels are formed between the skin, plaster 24B and safety strap 6B.

The same function can be achieved by the design shown in FIG. 6A, in which the cross-section of the safety strap 6A is bi-convex. The skin will yield and allow the surface of the safety strap to sink into the surface of the skin. The result is that almost no channels are formed between the skin, plaster 24A and safety strap 6A. The same operation is achieved with the design shown in FIG. 6C, in which the cross-section has a substantially flat central surface so that almost no channels are fomed between the skin, plaster 24C and safety strop 6C.

Generally, the operation intended according to the invention is achieved if the height or thickness of the safety strap decreases continuously towards the lateral side edges of the safety strap. The thickness at the edges should be no more than about 0.5 mm, such as less than about 0.3 mm, and the maximal thickness of the safety strap should be about 1 mm.

Figure 5:
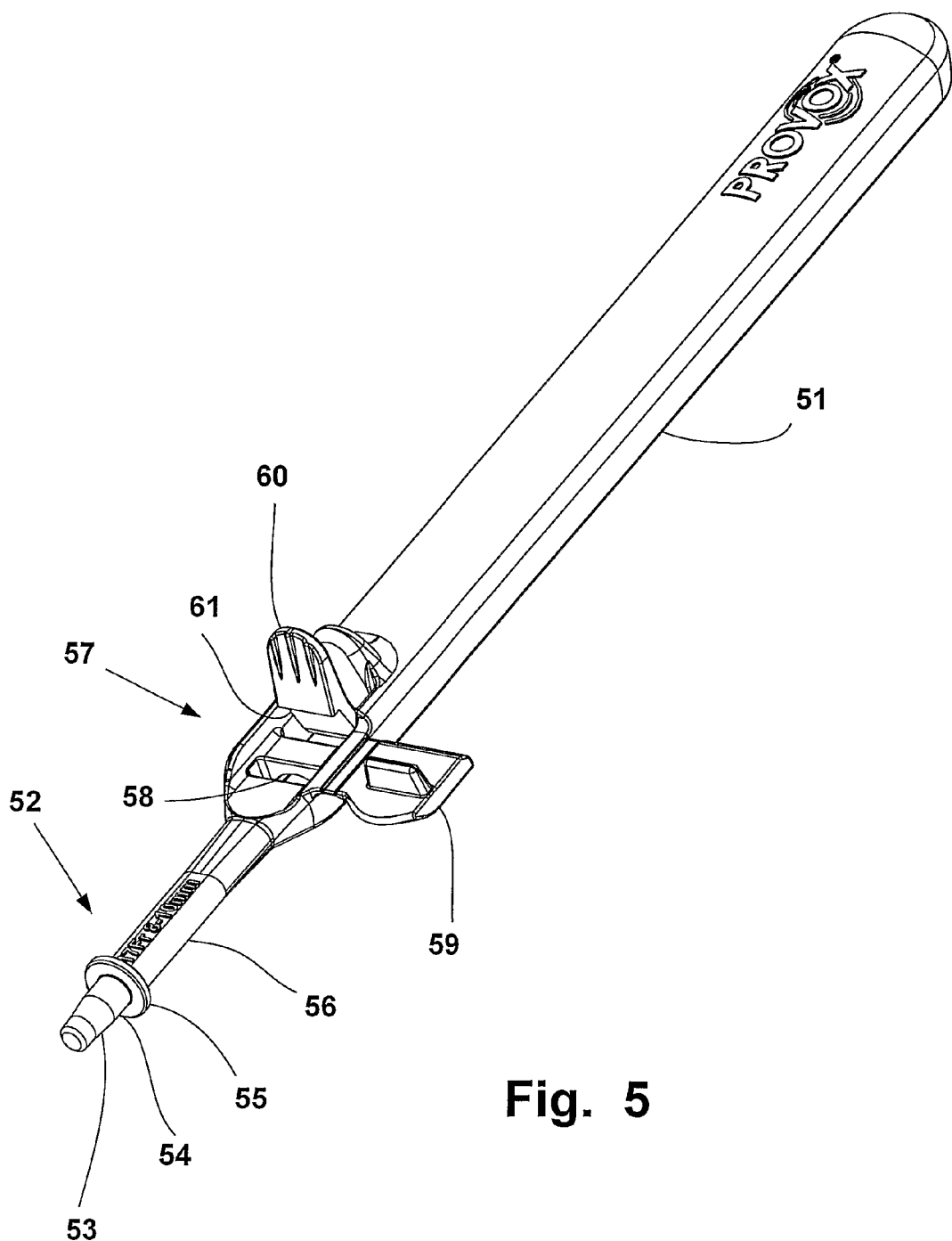
FIG. 5 is an elevation view of an embodiment of an insertion tool.

When the voice prosthesis should be put in place, an insertion tool 52 as shown in FIG. 5 may be used. The insertion tool 52 is designed for use by one hand, which means that the voice prosthesis is easy to put in place. The voice prosthesis may also be removed for cleaning or other purposes.

The insertion tool 52 is provided with a shaft portion 51 for gripping and operating the tool by one hand of the user. At the opposite end, the tool is provided with members for engaging and gripping a voice prosthesis. Thus, the outer end is provided with an engagement portion having a design corresponding to the inner dimensions of the tubular body portion. The outer end comprises a conical portion 53 followed by a cylindrical portion 54 and an end wall 55. The conical portion 53 engages the support ring and the cylindrical portion 54 engages the proximal portion of the tubular body portion. The wall 55 engages the proximal flange 4. The safety strap is passed along a second cylindrical portion 56 to a gripping portion 57. The gripping portion comprises a support surface 58 and a flap 59 which may be folded to position in which the safety strap is squeezed between the flap 59 and the support surface 58. The flap 59 is maintained in the last-mentioned position gripping the safety strap by means of a snap member 60 having a snap shoulder 61 interfering with the flap 59.

Figure 7:
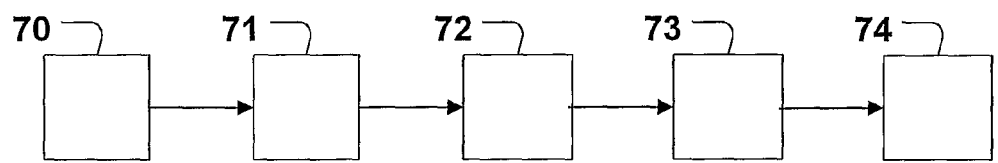
FIG. 7 is a flow chart illustrating an embodiment of an insertion method.

In use, the insertion tool is operated by one hand only of the user. First, the user in step 70, see FIG. 7, places the voice prosthesis in the correct position at the insertion tool and moves the flap 59 to the position gripping the safety strap and the snap member 60 maintains the flap 59 in this position. In step 71, the user operates the insertion tool to position the voice prosthesis in the correct position in the fistula. In step 72, the snap member 60 is activated by a finger of the same hand as is holding the insertion tool. In step 73, the insertion tool is removed and the safety strap is fixed by a plaster. Finally, in step 74, the user attaches the safety medallion to the skin of the user beside the filter 21 or at a convenient position. Now, the voice prosthesis is ready for use.

In this way, the device may be easily removed by the user for cleaning. At removal, the user makes free the safety medallion and pulls out the voice prosthesis by the safety strap. Re-insertion is also easily done by the user.

Herein above, an embodiment of the voice prosthesis has been described for elucidating the invention. However, the different parts and members may have different forms and shapes and may be combined in other ways than exactly as described. For example, the safety strap may have another shape than being dome-shaped, for example having a conical or elliptical shape. It may also have thinner thickness on the lateral edge or even being V-shape at the lateral edges in order to ensure as little leakage as possible The safety strap is preferably attached to the neck around the tracheostoma by means of a plaster surrounding the stoma and holding a humid moist exchanger (HME) with integrated valve. The user may press on the HME in order to shut the HME valve, so that airflow from the lungs through the trachea is directed through the voice prosthesis, wherein the valve integrated in the prosthesis opens at a certain opening pressure. It would be a drawback if leakage occurs at the HME plaster assembly. If the HME is tight, a leakage may still occur along the safety strap, between the strap and the plaster. With the design according to the present invention, such leakage is mitigated or completely eliminated. The dome-shape of the safety strap supports a better fit of the plaster than conventional straps having rectangular shape and sharp edges, such as the device shown in U.S. Pat. No. 4,614,516. Such leakage deteriorates the efficiency of the voice prosthesis, as less airflow will pass through it and the voice control of the user is impaired.

Also, in-situ cleaning of the prosthesis is possible with suitable tools, e.g. a flushing device for flushing the inner lumen of the prosthesis when in place in the user (in-situ). Also, a brush may be used for both in-situ and ex-situ cleaning. Safety is provided during in-situ cleaning by the safety strap and the safety medallion. The plaster providing a retaining means for the HME is left in place. Only a HME cassette is removed from the retainer and probably replaced with a new.

The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units.

In the claims, the term "comprises/comprising" does not exclude the presence of other elements or steps. Furthermore, although individually listed, a plurality of means, elements or method steps may be implemented by e.g. a single unit.

Additionally, although individual features may be included in different claims, these may possibly advantageously be combined, and the inclusion in different claims does not imply that a combination of features is not feasible and/or advantageous. In addition, singular references do not exclude a plurality. The terms "a", an "first", "second" etc do not preclude a plurality. Reference signs in the claims are provided merely as a clarifying example and shall not be construed as limiting the scope of the claims in any way.

Although the present invention has been described above with reference to a specific embodiment, it is not intended to be limited to the specific form set forth herein. Rather, the invention is limited only by the accompanying claims and, other embodiments than the specific above are equally possible within the scope of these appended claims.

The invention claimed is:

1. An insertion tool for inserting a tracheostoma voice prosthesis member into a fistula between oesophagus and trachea, comprising:
  an engagement portion for engaging and retaining said voice prosthesis member to be inserted into the fistula;
  a gripping portion for gripping a safety strap of said voice prosthesis member in a firm grip, the gripping portion comprising a support surface and a flap, wherein the safety strap is to be held between the support surface and the flap;
  a shaft portion adapted to be held by one hand of a user;
  a release lever arranged adjacent said shaft portion for operation by a finger of the same hand that is holding said shaft portion, wherein the release lever comprises a shoulder constructed to hold the flap in place so that the safety strap is held in the gripping portion between the support surface and the flap;
  whereby said release lever, after said voice prosthesis member being positioned in place in said fistula by operation of said insertion tool by means of said shaft, is constructed to be depressed so that the shoulder no longer holds the flap in place.

\* \* \* \* \*

UNITED STATES PATENT AND TRADEMARK OFFICE
CERTIFICATE OF CORRECTION

PATENT NO. : 8,236,007 B2  
APPLICATION NO. : 11/813393  
DATED : August 7, 2012  
INVENTOR(S) : Jan-Ove Persson Page 1 of 1

It is certified that error appears in the above-identified patent and that said Letters Patent is hereby corrected as shown below:

In the Specification

At column 3, line 15:

Please replace "en" with "an"

At column 3, line 17:

Please replace "pr" with "or"

At column 7, line 35:

Please replace "fomed" with "formed"

At column 7, line 35:

Please replace "strop" with "strap"

Signed and Sealed this  
Twenty-second Day of October, 2013

Teresa Stanek Rea  
*Deputy Director of the United States Patent and Trademark Office*